United States Patent [19]

Manchester

[11] Patent Number: 5,053,020

[45] Date of Patent: Oct. 1, 1991

[54] APPLICATOR HAVING TWO CANNULAS

[75] Inventor: Michael J. Manchester, Mendon, Mich.

[73] Assignee: The Upjohn Company, Kalamazoo, Mich.

[21] Appl. No.: 506,604

[22] Filed: Apr. 6, 1990

[51] Int. Cl.⁵ .............................................. A61M 5/00
[52] U.S. Cl. .................... 604/239; 604/264; 604/275
[58] Field of Search .............. 604/187, 263, 264, 275, 604/239, 240, 241, 242, 243, 280

[56] References Cited

U.S. PATENT DOCUMENTS

| | | | |
|---|---|---|---|
| 79,742 | 7/1868 | Faloon | 604/275 X |
| 2,626,603 | 1/1953 | Gabriel . | |
| 3,008,570 | 11/1961 | Roehr et al. . | |
| 3,292,624 | 12/1966 | Gabriel et al. . | |
| 3,439,675 | 4/1969 | Cohen | 604/275 X |
| 3,486,503 | 12/1969 | Porter et al. | 604/275 |
| 3,821,956 | 7/1974 | Gordhamer | 604/264 |
| 3,882,849 | 5/1975 | Jamshidi . | |
| 4,059,112 | 11/1977 | Tischlinger . | |
| 4,296,747 | 10/1981 | Ogle . | |
| 4,313,440 | 2/1982 | Ashley . | |
| 4,405,322 | 9/1983 | Jessup . | |
| 4,692,142 | 9/1987 | Dignam et al. . | |
| 4,737,150 | 4/1988 | Beaumle et al. . | |
| 4,767,416 | 8/1988 | Wolf et al. | 604/239 |
| 4,850,970 | 7/1989 | Sutherland . | |
| 4,981,472 | 1/1991 | Ennis, III et al. . | |

*Primary Examiner*—John D. Yasko
*Attorney, Agent, or Firm*—Flynn, Thiel, Boutell & Tanis

[57] ABSTRACT

An applicator for administering a medication comprising a syringe having a syringe cylinder for receiving a plunger. The discharge end of the cylinder has an integral projecting base portion and a first reduced diameter, blunt-tipped cannula integral with and projecting from the base portion. A second cannula of reduced diameter and also having a blunt-tip, is detachably mounted on the base portion. The first and second cannulas have through bores which communicate with each other. A detachable protective cap is provided for covering at least the second cannula.

17 Claims, 1 Drawing Sheet

APPLICATOR HAVING TWO CANNULAS

This invention relates to an applicator comprising a first, relatively short, cannula which is insertable to a relatively short depth in the body to be treated, a second, relatively long cannula which is insertable to a relatively long depth in the body to be treated and a detachable protective cap for protecting the first and second cannulas. The applicator is particularly useful for administering a mastitis treatment medication to a cow so that the medication can be infused either (1) into the teat cistern by insertion of the long cannula through the entire length of the teat canal, or (2) into the teat canal by insertion of the short cannula into and partway through the teat canal.

DESCRIPTION OF THE PRIOR ART

U.S. Pat. No. 4,850,970 discloses a syringe assembly employing a single cannula and a two-part cap. A cannula can be inserted only partway into the teat canal or all the way into the teat cistern by removing only one or both parts of the cap, respectively. The cannula extends through an opening in the outer end wall of an elongated inner cap. A relatively short, outer cap covers the portion of the cannula that projects beyond the end wall of the inner cap. When only the outer cap is removed, only the projecting portion of the cannula is exposed for insertion into the teat canal. When both of the inner and outer cap parts are removed, the full length of the cannula is exposed for insertion through the teat canal into the teat cistern. However, the tip of the cannula may be exposed to contamination if the outer cap accidentally falls off or if the user's finger touches the tip of the cannula during the physical step of removal of the outer cap.

U.S. Pat. No. 3,292,624 discloses a syringe having a first needle extending therefrom and a second needle detachably mounted on the syringe and encircling the first needle so that the medication to be injected will flow in series through a bore in the first needle and then through a bore in the second needle. A protective cap covers the assembly of the first and second needles.

U.S. Pat. No. 3,882,849 discloses a soft tissue biopsy device comprising a syringe having a sample-receiving hollow needle extending therefrom and a hollow needle-mounting shaft disposed within the needle and having internal passage means so that fluids can pass through the needle-mounting shaft into the syringe.

U.S. Pat. No. 4,737,150 discloses several embodiments of syringes, each having two cannulas which are disposed so that the medicament flows in series through bores in the cannulas. The cannulas are protected by a protective cap.

U.S. Pat. Nos. 4,296,747 and 4,405,322 also disclose syringes having two needles or catheters and a protective cap therefore.

SUMMARY OF THE INVENTION

According to the invention, there is provided an applicator for administering a medication which comprises an elongated syringe having a first, blunt-tipped cannula extending longitudinally from one end of said syringe and having a first, longitudinally extending bore therethrough. A second, blunt-tipped cannula is detachably mounted on the syringe. The second cannula has an inner sleeve section which encircles the first cannula and a blunt-tipped, hollow member which extends beyond the outer end of the first cannula. The hollow member has a longitudinally extending second bore which is coaxial with and constitutes an extension of the first bore in a direction extending away from the syringe. The first and second bores thereby provide a continuous flow path for the medication, which path extends from the syringe to the outer end of the second bore. A detachable protective cap covers the blunt tip of the second cannula so that the contents of the syringe are protected from contamination and the cannulas are sealed against leaks.

According to a preferred embodiment of the invention, there is provided an applicator for administering a mastitis treatment medication to a cow which comprises an elongated, mastitis medication-infusion syringe having a first, inner cannula projecting longitudinally from one end of the syringe. The first inner cannula comprises a first base portion which is joined to the syringe and which has a first outer end face, and a first, relatively short, tubular wall extending longitudinally away from the first outer end face. The first outer end face is adapted to abut against the distal end of a teat of a cow so that the first base portion cannot enter into the teat canal. The first tubular wall portion has a first, blunt, outer end so that it cannot readily penetrate the flesh of a cow. The first tubular wall portion has a diameter sized for fitting within the teat canal of a cow and has a length shorter than the length of the teat canal of the cow. Further, the first base portion and the first tubular wall portion have a first through bore extending longitudinally therethrough. A second, outer cannula is comprised of a second base portion which is detachably connected to the first base portion of the first inner cannula. The second cannula has an axially outwardly projecting boss having a second outer end face. The second outer cannula also includes a second, relatively long, tubular, tapered sidewall portion extending longitudinally away from the boss. The second base portion and boss cover and enclose the first base portion and the first sidewall portion of the first cannula and extend longitudinally therebeyond in a direction away from the syringe. The second outer end face is adapted to abut against the end of a teat of a cow so that the boss cannot be inserted into the teat canal. The second sidewall portion has a second, blunt, outer end so that it cannot readily penetrate the flesh of a cow. The second sidewall portion has a diameter sized for fitting within the teat canal of the cow and a length at least substantially as long as the length of the teat canal of the cow so that the medication can be infused directly into the teat cistern. The second sidewall portion has a second through bore extending longitudinally therethrough. The first and second through bores are coaxial and communicate with each other so that the second through bore constitutes an extension of the first through bore in a direction extending away from the syringe so that the first and second through bores provide a continuous flow path for the medication from the syringe to the outer end of the second through bore. A detachable protective cap covers the entire length of at least the second sidewall portion of the second cannula. The cap has an outer end wall for sealing the outer end of the second through bore and a tubular sidewall surrounding the second sidewall portion of the second cannula, with the inner end of the cap being detachably secured to the second boss of the second cannula.

DESCRIPTION OF PREFERRED EMBODIMENT

Figure 1:
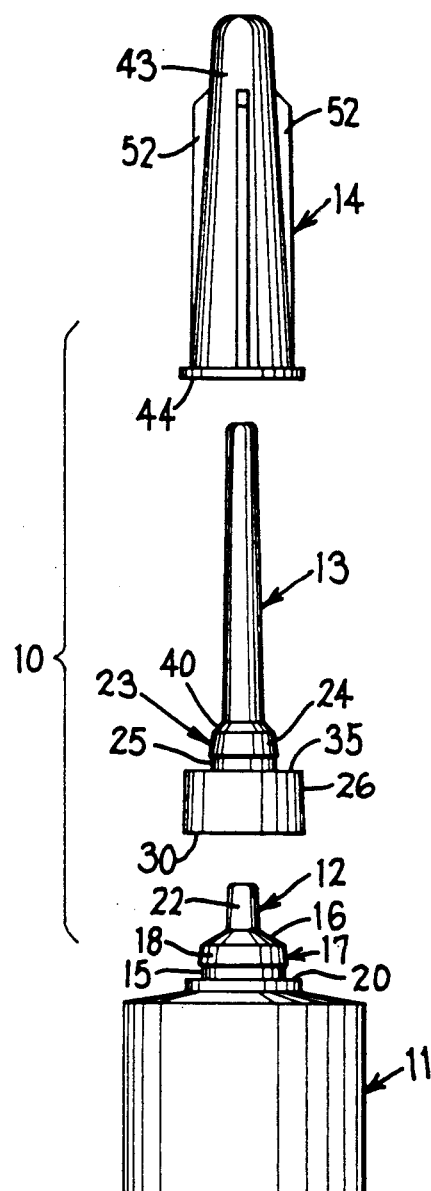
FIG. 1 is an exploded view of the applicator according to the present invention.

Referring to the drawings, the applicator 10, according to the invention, generally comprises an elongated container 11 having a first, inner, relatively short cannula 12 extending longitudinally from one end of the container, a second, outer, relatively long cannula 13 extending longitudinally from the short cannula 12, and a cap 14 covering at least the tubular sidewall portion of the long cannula 13.

Figure 2:
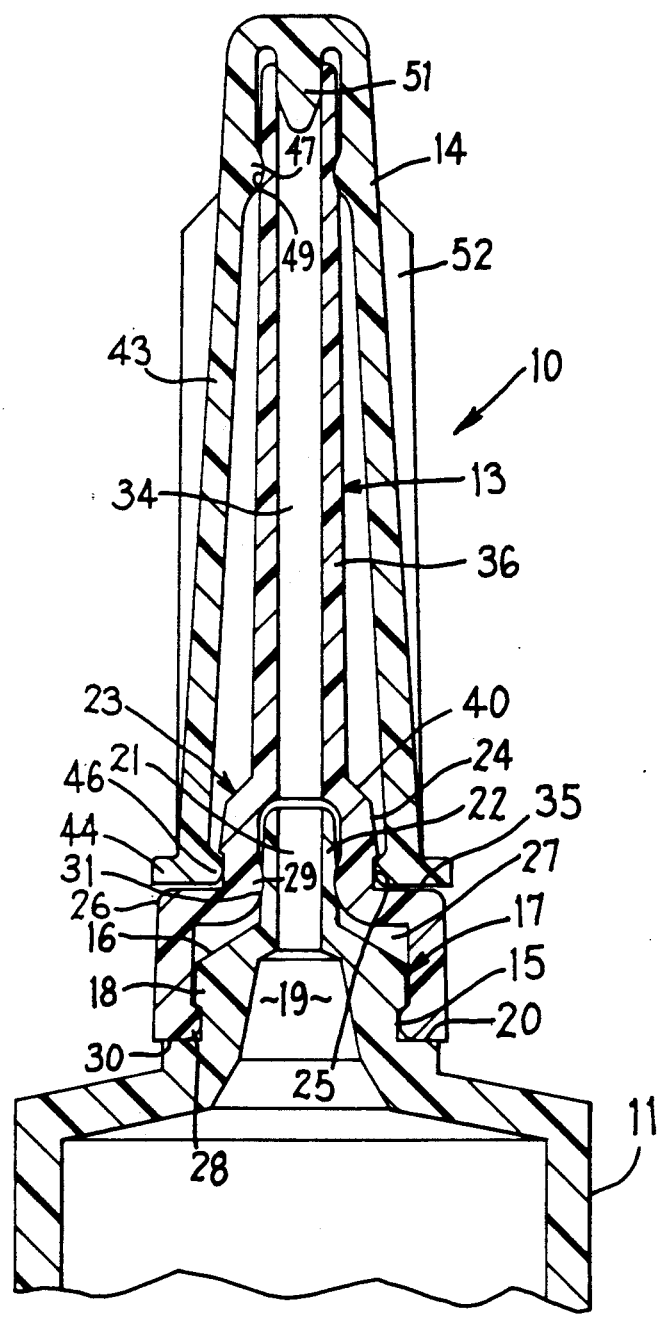
FIG. 2 is a longitudinal, central sectional view, on an enlarged scale, of the applicator.

The container 11 can be of any type suitable for parental administration of veterinary pharmacological compositions and is of a size sufficient for holding the required dosage of the veterinary pharmaceutical composition. For example, the container 11 can be a sterile, disposable, hypodermic syringe barrel made of low-density polyethylene. The first cannula 12 comprises an integral, axially outwardly extending hub or base portion 17 at the upper end of the container 11. The hub 17 has an upwardly tapered outer wall 16. The tapered outer wall 16 is sized so that it will abut against the distal end of a teat of a cow and will not enter the teat canal. The short cannula 12 comprises a first, relatively short, tubular wall portion 22 which projects upwardly from the central portion of the tapered outer wall 16. The hub 17 has a laterally outwardly projecting, annular rib 18 on the external surface thereof, and it has a central opening or through bore 19 (FIG. 2) extending longitudinally therethrough. The hub 17 has a flat wall 20 which is spaced downwardly a short distance from the rib 18 to define a circumferential groove 15 therebetween. The opening 19 communicates with the interior chamber of the container 11. The wall portion 22 of the cannula 12 is coaxial with the container 11 and extends axially from the hub 17 in a direction away from the container 11. The wall portion 22 of the cannula 12 is an elongated, smooth-surfaced tubular member having a blunt tip or outer end so that it cannot readily penetrate the flesh of a cow. The inner or lower end of the wall portion 22 is joined to the tapered outer wall 16 of the hub 17, which tapered wall is adapted to abut against the distal end of the teat of a cow. The wall portion 22 of the cannula 12 has a central through bore 21 extending lengthwise from the opening 19 in the hub 17. The bore 21 is open at its longitudinally outer end. The inner end of the bore 21 communicates with the opening 19 in the hub 17 and thence with the interior chamber of the container 11 so that the contents of the container 11 can be dispensed through the cannula 12. The wall portion 22 of the cannula 12 has a length suitable for the intended short penetration of cannula 12 into the teat canal of the cow to be treated. Typically, when the distal end of the teat abuts against the wall 16, the wall portion 22 of the short cannula 12 extends into the distal end of the teat canal a distance of about 4 mm. The diameter of the wall portion 22 of the cannula 12 is such that it can fit snugly within the distal portion of the teat canal of a cow. For example, the external diameter of the cannula 12 can be about 2.5 mm.

The container 11, hub 17 and wall portion 22 preferably are sections of a one-piece, monolithic, molded shape made of low-density polyethylene.

The second, outer, relatively long cannula 13 is a generally cylindrical, elongated, smooth-surfaced member having a laterally enlarged, inner section or second base portion 26 surrounding and releasably secured to the hub 17 of the short cannula 12. The inner section 26 of long cannula 13 has an internal cavity 27 for receiving therein the hub 17. The long cannula 13 comprises a boss 23 which projects axially outwardly from the inner section 26 and which receives the wall portion 22 of the short cannula 12 therein. The outer surface of the boss 23 has an annular enlargement 24 defining an annular groove 25. The long cannula 13 comprises a second, relatively long, tubular sidewall portion 36, which preferably tapers in a direction away from the container 11 at a small angle, for example, about one degree, relative to the longitudinal axis of the long cannula 13, in order to facilitate insertion and removal of the long cannula 13 in the teat canal of a cow. The enlarged inner section 26 of the long cannula 13 has an annular, laterally inwardly projecting ridge 28 at its longitudinally inner end. An end wall 30 is provided on the enlarged inner section 26 and said end wall is adapted to abut against the flat wall 20 of the hub 17. The inner section 26 also has a laterally inwardly enlarged ridge 29 which is adapted to sealingly engage the external wall of the wall portion 22 therebetween. When the long cannula 13 is releasably secured to the hub 17 of the short cannula 12, the end wall 30 of the long cannula 13 abuts against the flat wall 20 of the hub 17 and the ridge 28 underlies the rib 18 in order releasably to secure the long cannula 13 to the hub 17 by a snap-lock effect. In this position of the parts, the ridge 29 sealingly contacts the external surface of the wall portion 22 of the short cannula 12 in order to prevent leakage. The ridge 29 elastically deforms the area wall portion 22 that it contacts to form a shallow groove 31.

The inner section 26 of the long cannula 13 has a flat, external shoulder 35 for engaging the inner end of the cap 14. A through bore 34 is provided in the long cannula 13. The inner end of the bore 34 is coaxial with, is of substantially the same diameter as and constitutes a lengthwise extension of the bore 21 in the short cannula 12. The boss 23 of the long cannula 13 has a tapered shoulder 40 for engaging the distal end of a teat of the cow. The tapered shoulder 40 is sized so that it abuts against the distal end of the teat and does not enter the teat canal. The length of the wall portion 36 of the relatively long cannula 13, not including the inner section 26 and boss 23, is such that said wall portion will extend to, and preferably a short distance into, the teat cistern of the cow when the distal end of the teat contacts the tapered shoulder 40. For example, the wall portion 36 beyond the shoulder 40 can have a length of about 24 mm.

The cap 14 has an elongated, tubular sleeve portion 43 which is sleeved on the long cannula 13. The cap has a flange 44 at its inner end, which flange is adapted to abut against the flat external shoulder 35 of the inner section 26 of the long cannula 13. The cap 14 covers the full length of the long cannula 13, excluding the inner section 26. The sleeve portion 43 preferably is of such a length that it can be gripped between the thumb and index finger of the user in order to remove the cap 14, and those fingers will not extend beyond the flange 44 so as to prevent touching and contaminating the exposed cannula tip. The flange 44 has a laterally inward extension defining an annular ridge 46 which is releasably received in the groove 25 and presses lightly against the external surface of the boss 23 adjacent to the shoulder 35. This releasably locks the cap 14 in place and, also, improves the sealing effect by pressing ridge 29 against the wall of the sidewall portion 22 of the short cannula 12. The sleeve portion 43 is radially outwardly spaced from the sidewall portion 36 of the long cannula 13 throughout most of its length.

The inner surface of the axially outer portion of the cap 14 has an annular, laterally inwardly projecting, sealing ring 47 which contacts and resiliently deforms the opposing portion of the external surface of the axially outer portion of the sidewall portion 36 whereby to form a complementary groove 49 therein. In this way, the ring 47 and groove 49 provide an effective resilient seal between the cap 14 and the axially outward end portion of the long cannula 13. This serves to prevent leakage of the contents of the container 11 and to keep those contents sterile.

The cap 14 is closed at its outer end and it covers the open, axially outer, blunt end of the cannula 13. A post 51 projects axially from the inner surface of the cap 14 and is slidably receivable in the bore 34 of the long cannula 13 for releasably sealing the outer end of the bore 34. The cap 14 has a plurality of circumferentially spaced, axially extending ridges 52 on its outer surface so that the cap 14 can be manually gripped and removed.

When the contents of the container 11 are to be dispensed, in order to use the long cannula 13, the user will manually grip the ridges 52 on the sleeve portion 43 of the cap 14 between the thumb and index finger, then twist and pull off the cap 14 from the long cannula 13 in the lengthwise direction, whereby the entire length of the long cannula 13 becomes exposed and the contents of the container 11 can be dispensed. When the cap 14 and the long cannula 13 are both to be removed so as to expose the short cannula 12, the user will grasp the sleeve portion 43 and flex both the cap 14 and the long cannula 13 sidewardly to disengage the ridge 28 from rib 18 and then slide the assembly of the long cannula 13 and the cap 14 axially off the short cannula 12. The annular groove 25 and its cooperating ridge 46 are designed so that less force is required to separate them than the force required to separate the ridge 28 from groove 15. Thus, the cap 14 can be removed more easily than the long cannula 13 and the long cannula will remain in place when the cap is removed. For example, the groove 15 can be made to have a greater depth than groove 25 so that more force is required to remove ridge 28 from groove 15.

The container 11, the short cannula 12 and the long cannula 13 are preferably made of low-density polyethylene having a density of from about 0.91 to about 0.94. The cap 14 is made of either low-density polyethylene or high-density polyethylene having a density of about 0.940 to about 0.965. Because high-density polyethylene has a higher strength and hardness than low-density polyethylene, when the cap 14 is made of high-density polyethylene and it is placed on the axially outer end of the long cannula 13 and then is pushed axially inwardly thereon, the sealing ring 47 on the cap 14 will elastically deform successive portions of the external wall of the end portion of the long cannula 13 as it moves therepast until flange 44 abuts against the shoulder 35. In that position, the ring 47 forms the groove 49 and the opposing wall portions of said ring and groove resiliently press against each other to provide a tight seal between those parts, whereby to releasably hold the cap 14 in place. When the cap 14 is made of low-density polyethylene, the ring 47 will be resiliently flattened more and the groove 49 will be less deep, but the opposing walls of the ring 47 and groove 49 will still press against each other to form a tight seal between the cap 14 and the long cannula 13.

When the cap 14 is secured to the outer end of the long cannula 13 and said long cannula 13 is connected to the hub 17, both of the short cannula 12 and the long cannula 13 are protected from exposure and contamination and the entire applicator unit 10 can be safely stored and transported. When the pharmaceutical composition in the container 11 is to be administered, the cap 14 can be removed, or both of cap 14 and the long cannula 13 can be removed, as discussed above. If a relatively shallow depth of penetration of the short cannula is desired, both of cap 14 and long cannula 13 are removed so that the short cannula 12 can be inserted until the shoulder 16 abuts against the distal end of the teat of the cow. The shoulder 16 limits the depth of penetration of the cannula into the teat canal. When it is desired to provide a further depth of penetration, then only the cap 14 is removed, whereby the entire length of the long cannula 13 is exposed and the cannula can be inserted into the animal to the maximum extent.

The detachable protective cap 14, according to the invention, seals the contents of the syringe and protects the cannulas 12 and 13 from damage and contamination during storage, shipment and use. It permits the cannulas to be inserted into the body of the animal to various depths, as needed for proper administration of the veterinary pharmaceutical composition.

Although a particular preferred embodiment has been illustrated and described, the invention contemplates such changes as lie within the scope of the appended claims.

The embodiments of the invention in which an exclusive property or privilege is claimed are defined as follows:

1. An applicator for administering a medication, comprising: an elongated syringe having a first, blunt-tipped cannula extending longitudinally from one end thereof, said first cannula having a longitudinally extending first bore; a second, blunt-tipped cannula detachably mounted on said syringe, said second cannula having a sleeve section which encircles said first cannula and a blunt-tipped wall portion which extends beyond the outer end of said first cannula, said sleeve section having an inwardly enlarged ridge which sealingly engages against an outer peripheral surface of said first cannula in surrounding relationship to said first bore, said wall portion being coaxial with said first cannula and having a longitudinally extending second bore which is coaxial with and constitutes an extension of said first bore in a direction extending away from said syringe whereby said first and second bores provide a continuous flow path for said medication from said syringe to the outer end of said second bore; and a detachable protective cap covering the tip of said wall portion and extending longitudinally therefrom to said sleeve section and surrounding said sleeve section so that the contents of the syringe are protected from contamination, said cap including a further, annular ridge which projects inwardly to slidably and sealingly engage an outer peripheral surface of said sleeve section, said further ridge being in substantially longitudinally aligned and surrounding relationship relative to said first-mentioned ridge to reinforce the sealing engagement between said second cannula and said first cannula, said first cannula being elastically deformed by said first-mentioned ridge to define in the outer peripheral surface of said first cannula a complementary groove which cooperates with said first-mentioned ridge to effect a sealing engagement between said first cannula and said second cannula.

2. An applicator as claimed in claim 1, in which said first cannula is relatively short, said second cannula is relatively long and said cap is releasably attached to said syringe and covers the entire length of at least said second cannula.

3. An applicator as claimed in claim 1, including a snap-lock joint for releasably connecting said second cannula to said first cannula, said snap-lock joint being located adjacent to the inner ends of said first and second cannulas.

4. An applicator as claimed in claim 3, in which said snap-lock joint comprises a laterally inwardly extending annular lock ring at the inner end of said second cannula, and a cooperating sealing groove on the exterior surface of said first cannula.

5. An applicator for administering a mastitis treatment medication to a cow, comprising: an elongated, mastitis medication-infusion syringe having a first inner cannula projecting longitudinally from one end of said syringe, said first inner cannula comprising a first base portion joined to said syringe and having a first outer end face, said first inner cannula having a first, relatively short, tubular, sidewall portion extending longitudinally away from said first base portion, said first outer end face of said first base portion being adapted to abut against the end face of a teat of a cow so that said first base portion cannot be inserted into the teat canal of said teat, said first sidewall portion having a first blunt end at its outer end so that it cannot readily penetrate the flesh of the cow, said first sidewall portion having a diameter sized for fitting within the teat canal of the cow and having a length shorter than the length of the teat canal of the cow, said first base portion and said first sidewall portion having a first through bore extending longitudinally therethrough; a second, outer cannula comprising a second base portion detachably connected to said first base portion of said first inner cannula and having a second, outer, boss having a second, outer end face, said second, outer cannula having a second, relatively long, tubular, tapered, sidewall portion extending longitudinally away from said boss, said boss covering and enclosing said first sidewall portion and extending longitudinally therebeyond in a direction away from said syringe, said second outer end face being adapted to abut against the end of a teat of the cow so that said second boss cannot be inserted into the teat canal of said teat, said second sidewall portion having a second blunt tip at its outer end so that it cannot readily penetrate the flesh of the cow, said second sidewall portion having a diameter sized for fitting within a teat canal of the cow and having a length at least substantially as long as the length of the teat canal of the cow, said second sidewall portion having a second through bore extending longitudinally therethrough, said first and second through bores being coaxial and communicating with each other so that said second through bore constitutes an extension of said first through bore in a direction away from said syringe so that said first and second through bores provide a continuous flow path for said medication from said syringe to the outer end of said second through bore; a detachable protective cap for covering at least the entire length of said second sidewall portion of said second cannula, said cap being detachably secured to said boss of said second cannula, said cap having an outer end wall for closing the outer end of said second through bore and a tubular sidewall surrounding said second sidewall portion of said second cannula.

6. An applicator as claimed in claim 5, in which said second cannula extends to said first base portion and is releasably connected thereto by a snap-lock joint, said cap extending to and abutting against said second base portion and including an annular, internal, radially inwardly projecting ridge which slidably and sealingly engages the outer surface of said second boss.

7. An applicator as claimed in claim 5, in which said cap has an annular, internal, radially inwardly projecting ridge which slidably and sealingly engages the outer surface of said second sidewall of said second cannula.

8. An applicator as claimed in claim 7, in which the internal wall of said cap is radially spaced from the outer surface of said second sidewall of said second cannula from the location of said ridge to said second outer end face.

9. An applicator as claimed in claim 5, in which said cap has an internal axially extending post which extends into and closes the outer end of said second through bore.

10. An applicator as claimed in claim 5 in which the length of said cap is sufficiently large that it can be manually grasped between the thumb and index finger of the user and the thumb and index finger will be prevented from touching and contaminating the tip of the outer cannula.

11. An applicator as claimed in claim 1, wherein said second cannula is significantly longer than said first cannula, said first and second bores having respective outer and inner ends which are in closely adjacent and substantially adjoining relationship, said inwardly enlarged ridge of said sleeve section of said second cannula being sealingly engaged against said first cannula at a location spaced from said adjoining bore ends by a distance which is less than the length of said first cannula.

12. An applicator as claimed in claim 11, wherein said cap includes an inwardly projecting seal ring which contacts and resiliently deforms said wall portion of said second cannula adjacent the tip thereof to define therein a complementary groove which cooperates with said seal ring to effect a resilient seal between said cap and said second cannula.

13. An applicator as claimed in claim 12, wherein said cap includes an internal longitudinally extending post which extends into and closes the outer end of said second bore.

14. An applicator for administering a medication, comprising: an elongated syringe having a first, blunt-tipped cannula extending longitudinally from one end thereof, said first cannula having a longitudinally extending first bore; a second, blunt-tipped cannula detachably mounted on said syringe, said second cannula having a sleeve section which encircles said first cannula and a blunt-tipped wall portion which extends beyond the outer end of said first cannula, said wall portion being coaxial with said first cannula and having a longitudinally extending second bore which is coaxial with and constitutes an extension of said first bore in a direction extending away from said syringe whereby said first and second bores provide a continuous flow path for said medication from said syringe to the outer end of said second bore, said second cannula being significantly longer than said first cannula, said first and second bores having respective outer and inner ends which are in closely adjacent and substantially adjoining relationship, said sleeve section having an inwardly enlarged ridge which sealingly engages against said first cannula at a location spaced from said adjoining bore ends by a distance which is less than the length of said first cannula, said first cannula being elastically deformed by said ridge to define in said first cannula a complementary groove which cooperates with said ridge to effect a sealing engagement between said first cannula and said second cannula; and a detachable protective cap covering at least the tip of said wall portion so that the contents of the syringe are protected from contamination.

15. An applicator as claimed in claim 14, wherein said cap extends longitudinally from the tip of said wall portion of said second cannula toward said sleeve section in surrounding relationship to said wall portion, said cap including an inwardly projecting seal ring which contacts and resiliently deforms said wall portion adjacent the tip thereof to define therein a complementary groove which cooperates with said seal ring to effect a resilient seal between said cap and said second cannula.

16. An applicator as claimed in claim 15, wherein said cap includes an internal longitudinally extending post which extends into and closes the outer end of said second bore.

17. An applicator as claimed in claim 16, wherein said cap extends longitudinally from the tip of said wall portion to said sleeve section in surrounding relationship to said wall portion, said cap including an annular ridge which projects inwardly to sealingly engage an outer peripheral surface of said sleeve section, a portion of said cap between said seal ring and said annular ridge being radially outwardly spaced from said wall portion of said second cannula.

* * * * *